United States Patent
Lingenfelder et al.

(10) Patent No.: US 6,558,380 B2
(45) Date of Patent: May 6, 2003

(54) INSTRUMENT FOR SURGICAL PURPOSES AND METHOD OF CLEANING SAME

(75) Inventors: Christian Lingenfelder, Ulm (DE); Stephan Ertl, Ulm (DE); Stefan Strobel, Langenau (DE); Rudolf Rösch, Ichenhausen (DE); Siegfried Förster, Neu-Ulm (DE); Matthias Fryda, Braunschweig (DE); Lothar Schäfer, Meine (DE); Inga Tröster, Braunschweig (DE); Dennie Herrmann, Braunschweig (DE)

(73) Assignee: GFD Gesellschaft fur Diamantprodukte mbH, Ulm (DE)

( * ) Notice: Subject to any disclaimer, the term of this patent is extended or adjusted under 35 U.S.C. 154(b) by 0 days.

(21) Appl. No.: 09/732,862

(22) Filed: Dec. 8, 2000

(65) Prior Publication Data

US 2002/0072746 A1 Jun. 13, 2002

(51) Int. Cl.[7] ............................................. A61B 18/18
(52) U.S. Cl. .......................... 606/41; 606/51; 600/374
(58) Field of Search ................... 606/41, 42, 45, 606/46, 48–52; 600/372, 374

(56) References Cited

U.S. PATENT DOCUMENTS

| 4,492,231 | A | * | 1/1985 | Auth ............................ 606/40 |
|---|---|---|---|---|
| 5,352,493 | A | | 10/1994 | Dorfman et al. |
| 5,562,769 | A | | 10/1996 | Dreifus et al. |
| 5,697,926 | A | * | 12/1997 | Weaver ........................ 606/39 |
| 5,893,849 | A | * | 4/1999 | Weaver ........................ 606/39 |
| 6,048,341 | A | * | 4/2000 | Hirakawa et al. ............. 606/51 |
| 6,066,137 | A | | 5/2000 | Greep .......................... 606/45 |
| 6,074,387 | A | * | 6/2000 | Heim et al. ................. 128/898 |
| 6,080,378 | A | | 6/2000 | Yokota et al. |
| 6,162,219 | A | * | 12/2000 | Nilsson et al. ................ 606/41 |
| 6,413,255 | B1 | * | 7/2002 | Stern ........................... 606/41 |

FOREIGN PATENT DOCUMENTS

| EP | 0 994 074 A2 | 4/2000 |
|---|---|---|
| WO | WO 99/40858 | 8/1999 |
| WO | WO 00/44012 | 7/2000 |
| WO | WO 01/50964 A2 | 7/2001 |
| WO | WO 01/89402 A1 | 11/2001 |

* cited by examiner

Primary Examiner—Michael Peffley
(74) Attorney, Agent, or Firm—Young & Basile, P.C.

(57) ABSTRACT

An instrument for surgical purposes, especially for coagulation, is proposed. This instrument has at least one arm, the tips of the arms having electrical contact regions which can be electrically connected to a control unit for touching a tissue for the purpose of coagulation. The contact regions are formed from doped diamond to produce the electrical conductivity.

27 Claims, 11 Drawing Sheets

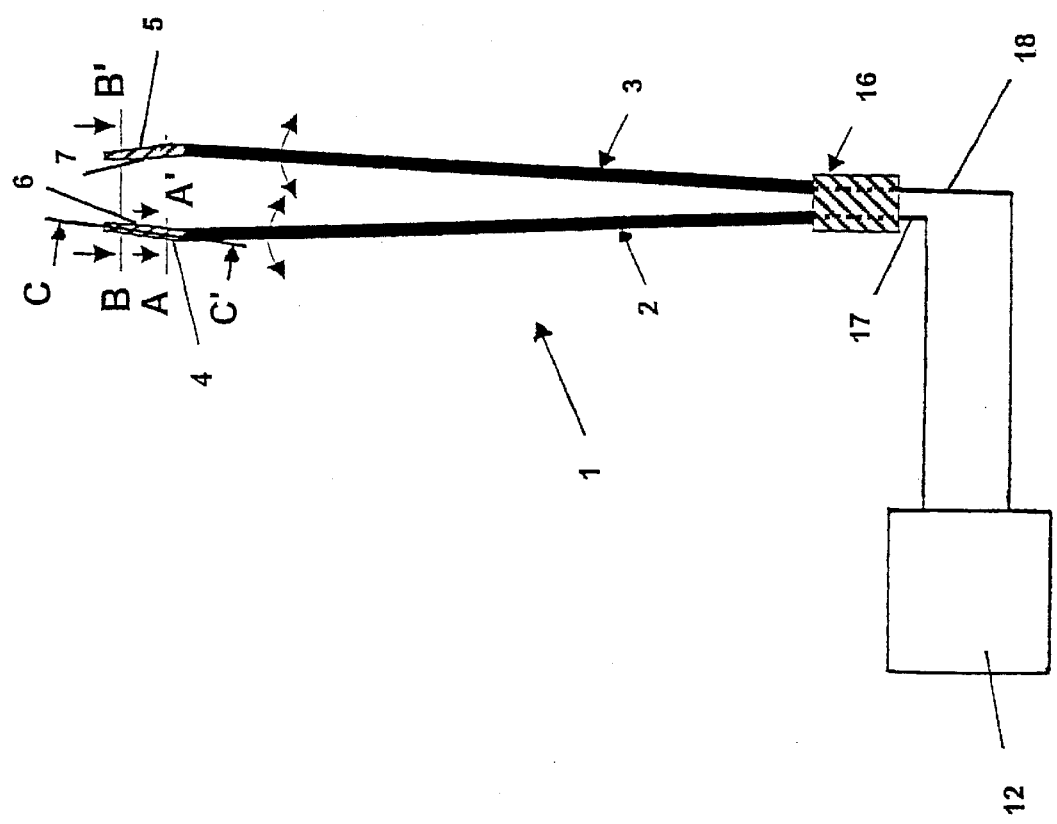

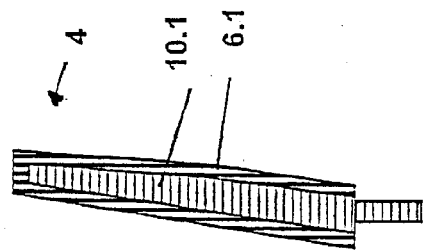
Fig. 2b (C-C')
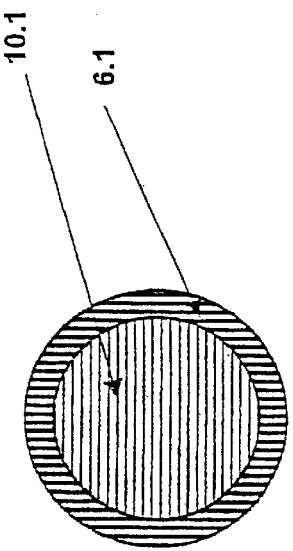
Fig. 2a (A-A')
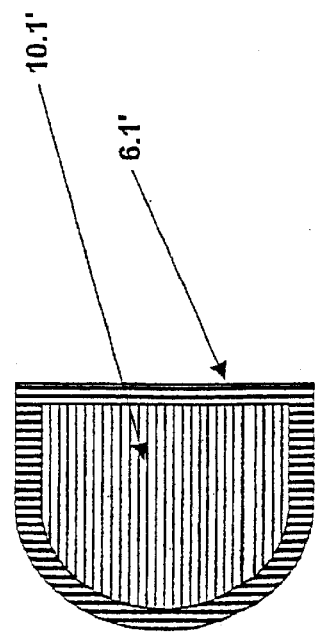
Fig. 2c (A-A')

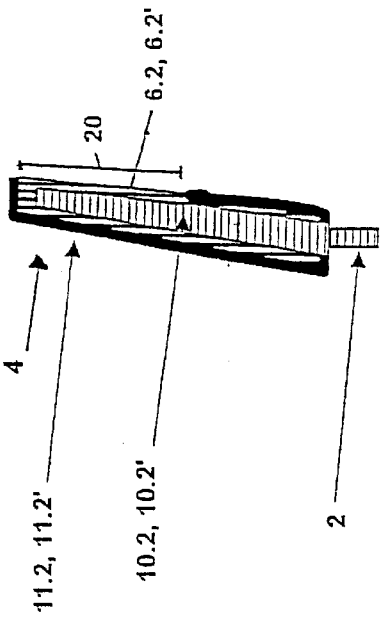
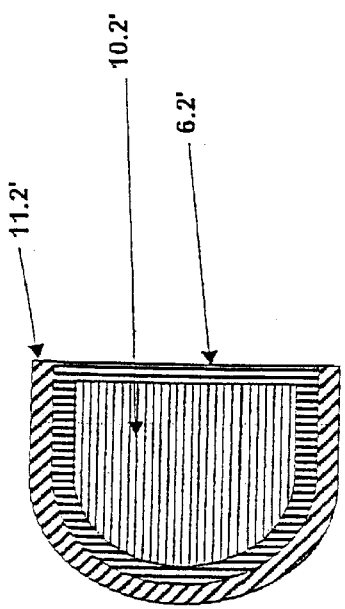
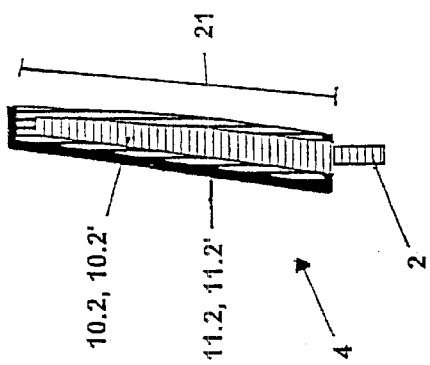
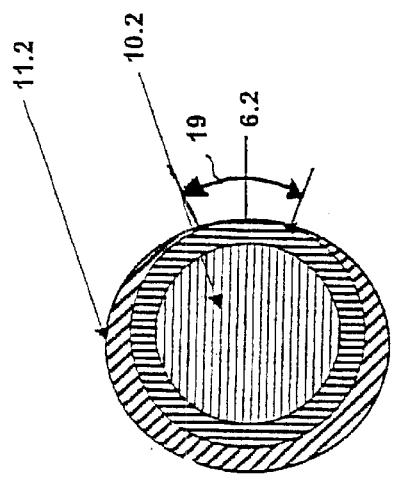

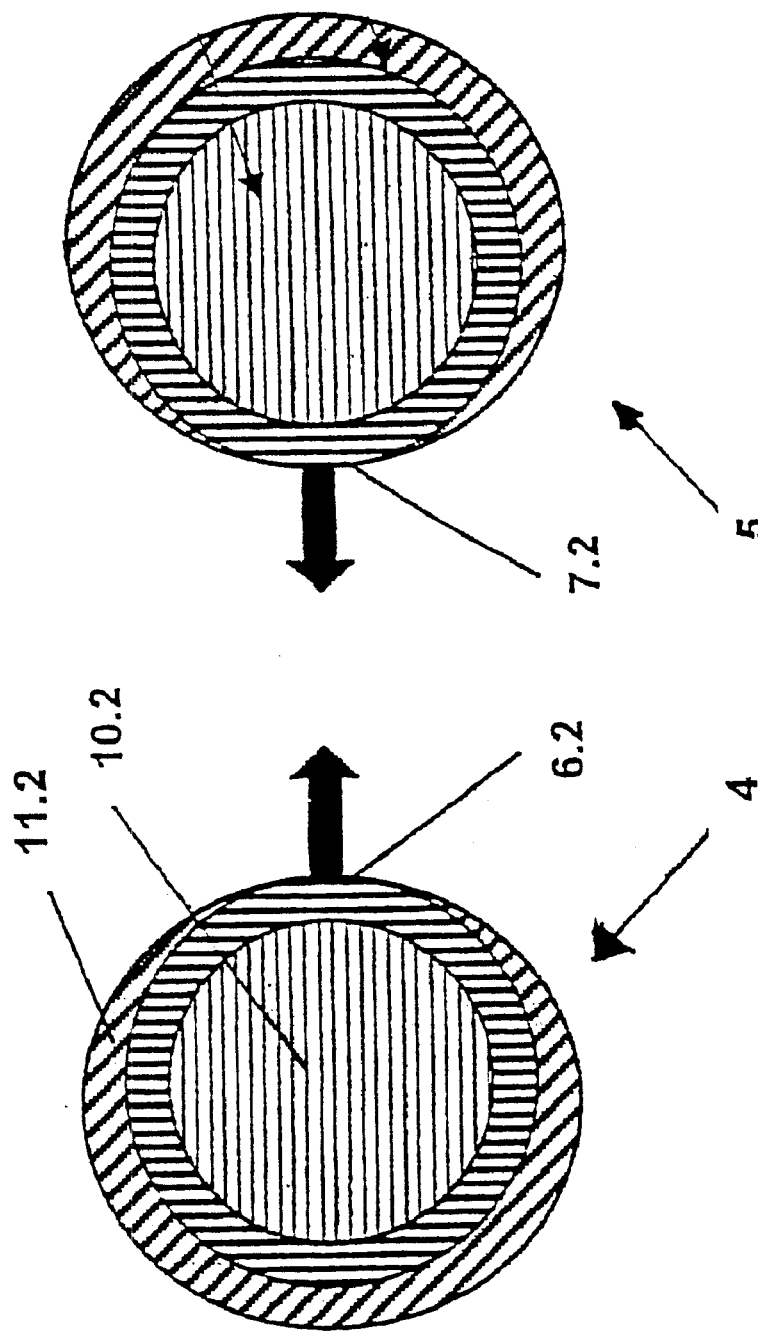

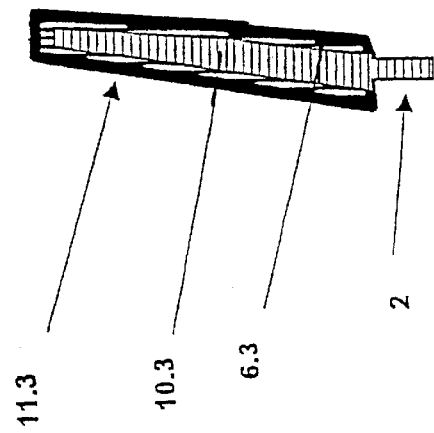
Fig. 4b (C-C')
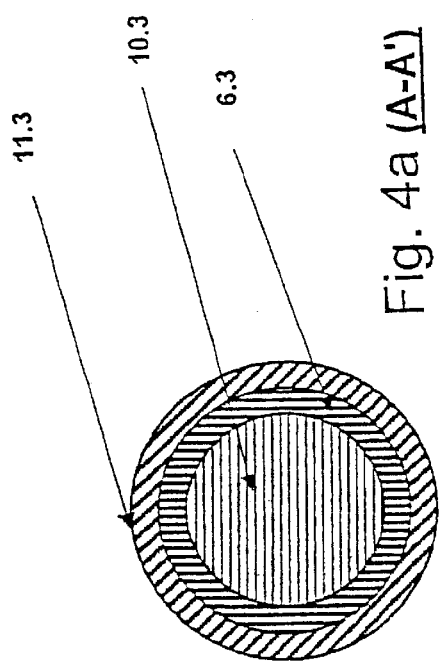
Fig. 4a (A-A')
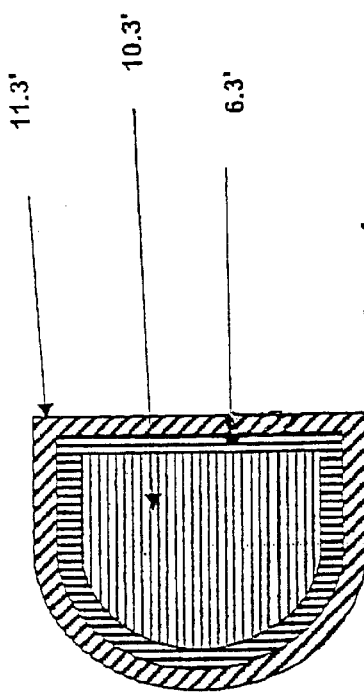
Fig. 4c (A-A')

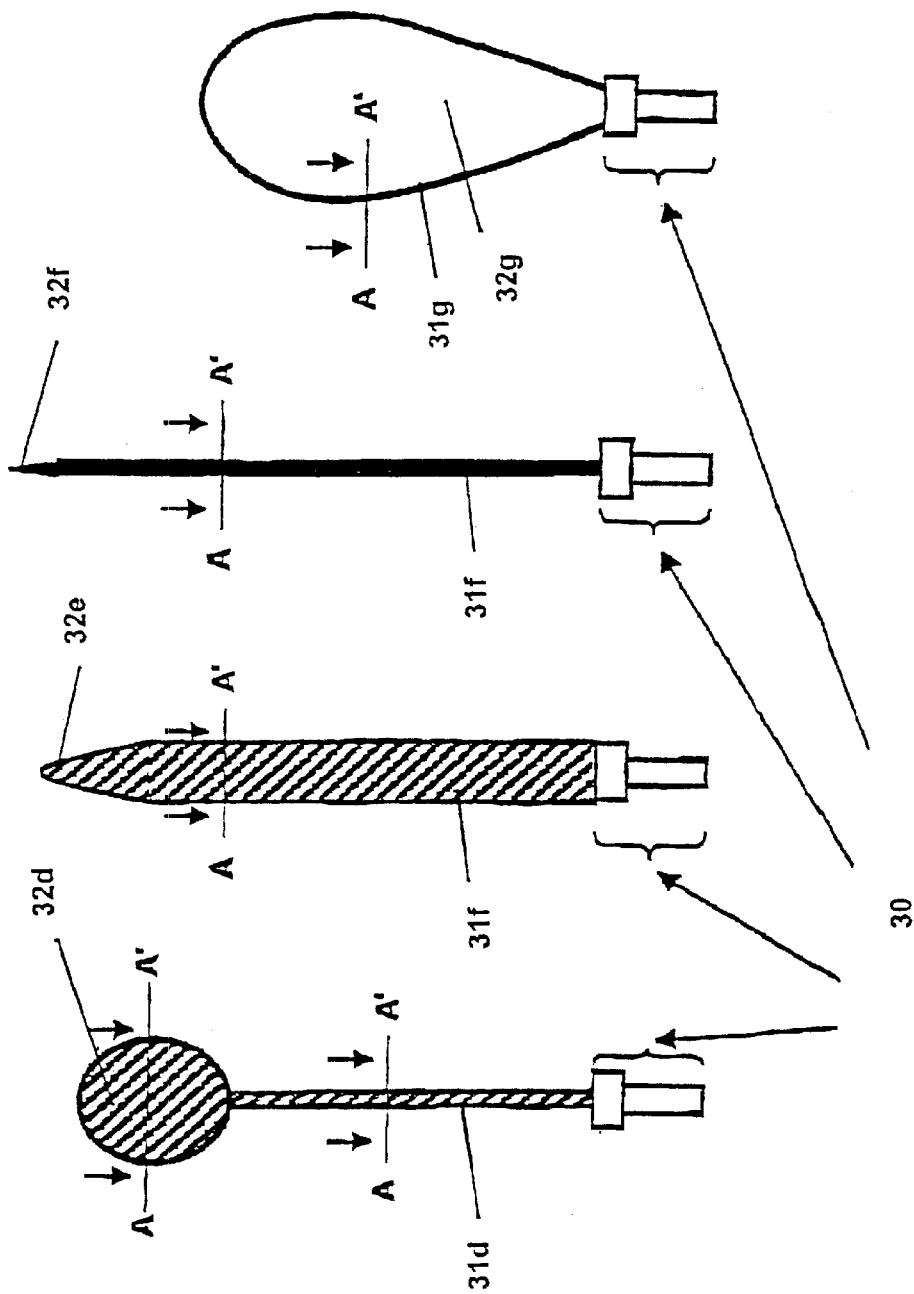

INSTRUMENT FOR SURGICAL PURPOSES AND METHOD OF CLEANING SAME

BACKGROUND OF THE INVENTION

The present invention relates to an instrument for surgical purposes, especially for coagulation, and to a method of cleaning said instrument.

In surgery or microsurgery, coagulation has a very wide field of indication. Conventionally coagulation is caused with the aid of forceps, tweezers, a wire or a blade to stop bleeding from open wounds. For example the bleeding vessel is pressed together with the forceps or tweezers and then a high-frequency current is led through the tip (bipolar application).

The high-frequency current can also be introduced into the surrounding tissue, e.g. via a blade. In this case a large-area electrode functions as a counterelectrode; current flows through the body, coagulation takes place in the region of the blade, i.e. the region of highest current density (unipolar application).

In both cases, the electrical resistance of the tissue causes conversion of the electrical energy into thermal energy and thus the heating up and coagulation of the tissue, i.e. the clotting of the cell substance.

Tweezers or forceps for surgical purposes are known, for example, which are suitable for unipolar and bipolar coagulation and have two arms moveable towards one another and which are electrically insulated from one another. These arms have at their tips electrical contact surfaces formed from metal. These electrical contacts are connected to a control unit. When a piece of tissue is touched/grasped between the two facing inner sides and a flow of current through the contacts or the tissue is activated, there is coagulation of the grasped tissue.

These surgical instruments according to prior art have a number of disadvantages.

Often, when metals are used, this results in undesired adhesion of the tissue to the metal surface, which in the worst case can cause the coagulated part to tear away again.

Moreover, the use of conventional surgical instruments having metal contact, surfaces is expensive, since after an operation the instruments are either thrown away or have to be expensively mechanically and chemically cleaned, there always being the risk that, e.g., tissue or blood residues remain.

A particularly high risk arises from the contaminated electrodes. Dried-on blood or tissue residues are here sufficient to electrically insulate the metal contact surfaces; this can lead first to circuit failure and than to sparking or carbonization of the contact surface and burning of the tissue on the contact surface. Moreover, additional risks arise where infectious tissue adheres.

Moreover, the limited thermal conductivity of the metal used can lead to irregular heating of the metal during the coagulation process and to the formation of local temperature peaks ("hot spots"). There is reason to suppose that burned tissue is produced and continues to adhere at these "hot spots" even in normal use. This means a dangerous loss of quality in tweezers according to prior art.

The heating capacity of metals can also have a disadvantageous effect, since through the residual heat stored in metal the coagulation process is possibly continued for longer than desired by the operator, such that there is undesired "inertia" of the instrument which can cause burns or adhesions, and this is very disadvantageous particularly in microsurgery.

SUMMARY OF THE INVENTION

The object underlying the present invention is, therefore, to create an instrument which overcomes the above-described disadvantages of conventional instruments, especially with respect to the production and elimination of adhesions.

This object is achieved in respect of the instrument of the present invention.

Because the contact regions consist of a diamond doped to produce electrical conductivity, the disadvantages of conventional contacts in respect of thermal conductivity, heat capacity, lacking inert properties or undesired adhesion, as well as contamination on the contact regions and difficulty of cleaning and irregular current conduction resulting therefrom are avoided. The coagulation can here occur either through direct contact of the tissue with the diamond electrode and the existing flow of current through the tissue, or through capacitive energy transmission, such as with an insulated electrode to which electricity is applied. In each case, above all, the capability of cleaning the contact regions or the instrument is greatly improved and the risk of adhesion of tissue reduced.

Diamond has the advantage that it is completely inert chemically and thus biocompatible. As a result of the physical structure, no diffusion of doping agents out of the diamond can occur. Thus, it can be used without hesitation in surgery. In addition to the inert properties of diamond at the surface of the contact region, the capacity of the diamond surface for termination (i.e. deliberate application of chemisorbed molecules or atoms—such as e.g. oxygen, fluorine (hydrophilic) or hydrogen (hydrophobic)—to the surface) renders possible the deliberate setting of the physical and chemical properties of the surface, such as its hydrophobicity/hydrophilicity. Through suitable termination of the surface, the adhesion of tissue can be further reduced or avoided.

The thermal conduction properties are also radically improved. This is due to the fact that diamond as an insulator and doped as a conductor has extraordinarily high thermal conductivity, which is even significantly higher than that of metals such as copper or silver. Thus, there is quickly uniform heat distribution within the contact region; no high temperature gradients occur which could cause the formation of a hot spot.

The thermal capacity of the diamond contact region can also be kept very low. Diamond has first of all a low specific heat capacity, which is practically independent of the doping. Moreover, diamond can be deposited in thin layers but nevertheless in a stable manner, such that a very low thermally active mass is produced.

The particular suitability of contact regions formed from highly doped diamond arises moreover from the fact that the electrical resistance of this material is largely independent of temperature. Admittedly, other semiconductor substances with a large band gap also show extensive independence of temperature in the temperature range of the application (e.g. SiC), but only diamond is simultaneously chemically inert.

A further great advantage of the diamond contact regions according to the invention arises from the fact that adhesions to the diamond which have possibly occurred anyway can be removed relatively simply. Diamond here shows good resistance to mechanical and aggressive chemical cleaning. Moreover, with the method according to the invention it is possible to clean the contacts electrolytically, without the electrode material being damaged. Thus the instrument according to the invention can be reused often and is thus economical and, environmentally friendly. Because of the possibility of reuse, in other places the instrument can also assume other high-grade embodiments which represent an improvement for the operator without any economic disadvantages arising.

The present invention has advantageous embodiments.

One advantageous embodiment provides for the contact regions to have an electrically conductive core. This core, which preferably consists of a (hard) metal or of materials often used in medicine such as niobium, iridium, tantalum, tungsten or titanium, is, on the one hand, mechanically able to bear a heavy load and on the other hand represents a good electrical conductor, which makes the connection with the contact region. The core can also consist of graphite, Zr or carbon-fibre-reinforced carbon. The deposition of diamond from a plasma leads to a chemical bond between the core material and the diamond layer. Thus very strong bonding of core-material and contact region is produced. CVD (chemical vapor deposition) methods are used here which are particularly suitable for coating three-dimensional materials. Special attention should be drawn to hot-filament CVD. This is very flexible in respect of the shape of the components to be coated (and can thus even be used for coating drills). In addition to hot-filament CVD, microwave plasma CVD and ECR-supported (electron cyclotron resonance) microwave CVD are also possible. Common advantages of these methods are good homogenous coating of three-dimensional components and high flexibility in respect of the shapes which can be coated.

However other embodiments of instruments which provide no electrically conductive core are also advantageous. Thus it is possible, for example, to produce the core of the arms of the instrument according to the invention from a material which is not electrically conductive and to coat this core over its full length, i.e. from the coagulation tip up to the connection contact for the voltage supply, with an electrically conductive layer, e.g. the doped diamond layer according to the invention. An insulating material can be applied to regions of this coating as required.

Moreover, additional embodiments of the invention are possible, for instance an electrically conductive or non-conductive diamond core. Furthermore, it is also possible to apply intermediate layers between any type of core and the doped diamond layer according to the invention. One embodiment provides for additional conductive layers to be applied at least in regions to the conductive doped diamond layer of the contact region. In this case, the diamond serves to avoid hot spots through improved heat distribution in the contact region.

An advantageous embodiment has proved to be that the concentration of doping agent in the contact region is more than $5 \times 10^{18}$ cm$^{-3}$. As particularly advantageous doping agents should be mentioned boron, sulphur, lithium or titanium; nitrogen, phosphorus or sp$^2$-bonded carbon are also possible in the diamond layer, for example. The initially outlined advantages here arise in a special manner in that the specific resistance of the doped diamond of the contact regions is lower than 100 Ohm cm, preferably lower than 1 Ohm cm, by particular preference lower than 0.01 Ohm cm, while the average layer thickness of the contact region is up to 300 micrometers, preferably less than 10 micrometers, by particular preference 1 to 5 micrometers. With these parameters it is guaranteed that the series resistance of the coating is low, such that negligible self-heating occurs; the sensible heat is moreover quickly passed to the surroundings through the high thermal conductivity and low heat capacity.

A particularly advantageous embodiment arises from the fact that the surgical instrument can be operated with control units according to prior art (i.e. no expensive new purchase of a control unit is necessary). However, the instrument can also be electrically connected to a special control unit according to the invention, which only represents a very small modification of those of prior art (this is supplemented by a "cleaning option", i.e. a voltage source is provided which serves as a voltage supply in the following electrochemical cleaning). In any case, both control units have a high-frequency generator to generate unmodulated and modulated high-frequency currents through the contact regions.

However, it is particularly advantageous that the control unit according to the invention has an immersing basin which can be filled with liquid for dipping the contact regions into this liquid, and a voltage source to apply a d.c. or a.c. voltage to the contact regions dipped into the liquid, or can be connected to the immersing, basin/voltage source. By this means, possibly even without rough mechanical prior cleaning, the diamond contact region can be electrochemically cleaned-of adhesions. This can, depending on the choice of the other method parameters, take place so thoroughly that e. g. subsequent additional steam sterilization can possibly be dispensed with (although this is still required by law in Germany).

It is particularly advantageous here if the voltage generated by the voltage source has an amplitude between 0 and 1000 V, preferably 0 to 10 V, by particular preference 1 to 5 V. The current density at the outer surfaces of the doped diamond contact regions is here advantageously up to 10 A per cm$^2$.

The electrochemical cleaning, which takes place on instrument arms dipped in a liquid containing distilled water (here, if two arms of a pair of tweezers are dipped, the contact regions of the two arms are disposed at a fixed spacing from one another), is improved in that in addition the liquid is mixed with additives, such as solvents, cleaning agents, disinfectants, acids (e.g. sulphuric acid) and other, even solid/soluble additives or additives which cause the electrical conductivity. In addition, the liquid can also be heated or have ultrasound applied to it in order to accelerate or improve the cleaning effect.

A further advantageous embodiment of the instrument provides for the contact regions, e.g. on the respective arms of a pair of tweezers, to have the same or opposite polarity and in a corresponding manner be thus connected to the control unit or be responded to. Thus it is also possible, both during operation and in the subsequent electrochemical cleaning, to proceed optionally in a unipolar or bipolar manner; the polarity of the same instrument can be different during a coagulation operation and during a cleaning operation.

BRIEF DESCRIPTION OF THE DRAWINGS

The present invention will now be explained with the aid of a number of figures. These show:

FIG. 1. a pair of tweezers according to the invention which is connected to a control unit, FIGS. 2a–2c sections through the tips of the arms of a pair of tweezers according to the invention, FIGS. 3a–3e sections through the tips of the arms of a further embodiment of a pair of tweezers according to the invention, FIGS. 4a–4c sections through the tips of the arms according to a further embodiment of a pair of tweezers according to the invention, FIGS. 4d–4g sections through the tips of the arms of further embodiments of surgical instruments according to the invention, FIGS. 5a, 5b the basic circuitry of a pair of tweezers according to the invention, in bipolar and unipolar operation, FIGS. 6a, 6b representations of the current flow in unipolar and bipolar operation, FIGS. 7a,7b the cleaning of a pair of tweezers in bipolar and unipolar operation, FIG. 8 electrolysis current-voltage curve for a pair of tweezers according to the invention.

DETAILED DESCRIPTION OF THE PREFERRED EMBODIMENT

Figure 5A:
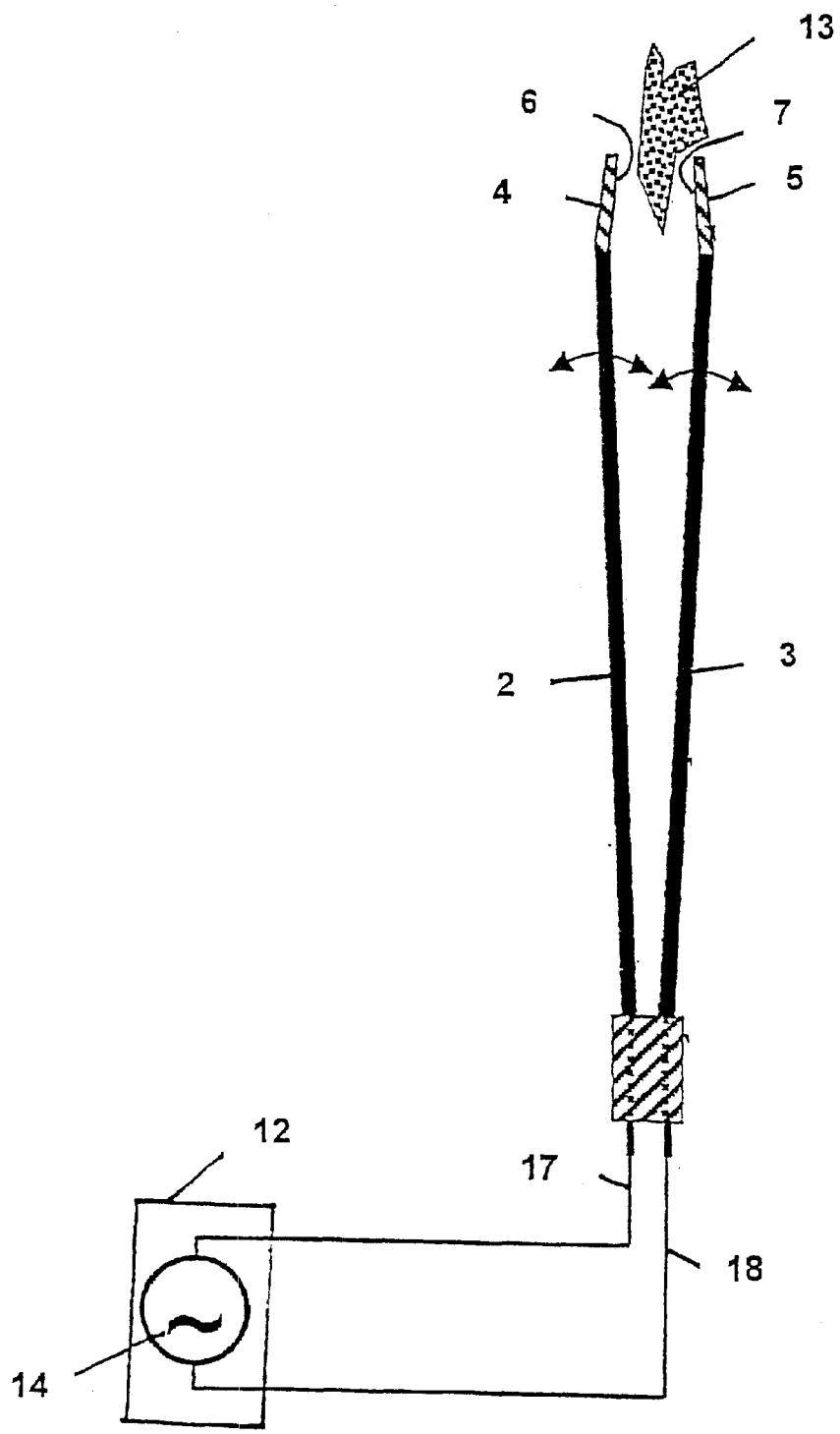

FIG. 1 shows a pair of tweezers 1 for surgical purposes, especially for coagulation, as an example of a surgical instrument. These tweezers have two arms 2 and 3, moveable towards one another and electrically insulated from one another. At its tip 4, arm 2 has (in areas) an electrical contact region 6 which consists of electrically conductive doped diamond. The facing arm 3 has correspondingly at its tip 5 a contact region 7 formed from the diamond doped to produce the electrical conductivity.

The electrical contact region 6 is connected to the control unit 12 through arm 2 via an electrical connection 17. Correspondingly, the contact region 7 of arm 3 is connected to the control unit 12 via an electrical connection 18. The support 16 and the arms 2 and 3 held therein have, in the region different from the arm tips, a covering or the like to electrically insulate arm 2 from arm 3.

The arms 2 and 3 can be moved towards each other such that a piece of tissue, not shown, can be grasped between the arm tips 4 and 5 and can have an electric current, generated in the control unit 12, passed through it for the purpose of coagulation. More exact details of the coagulation will be given more fully later (in particular in the description of FIGS. 5a, 5b, 6a, 6b).

FIGS. 2a to 2c show sections through the tip 4 of arm 2 (for arm tip 5 identical but mirror-inverted views arise; the same is true for drawings 3a to 3d and 4a to 4c).

FIG. 2a shows a section as per A–A' through the tip 4 of arm 2. The arm tip 4 contains an electrically conductive core 10.1. This core 10.1 is electrically connected to the control unit 12 via arm 2 or supply line 17 (the corresponding situation naturally arises also for arm 3). The doped diamond material forming the contact region 6.1 is applied to the core 10.1. In the present embodiment, the doped diamond material forming the contact region is disposed concentrically around the core 10.1 which is round in cross-section. The core is preferably formed from a refractory metal, preferably titanium, tungsten, niobium, tantalum or alloys of these metals. However, other substrate materials (silicon, silicon carbide, graphite, carbides of refractory metals, iridium or other materials with low lattice mismatch, semiconductors (e.g. Ge) or other core materials coated with same are possible according to the invention. The contact region 6.1 formed from doped diamond material is applied to the core 10.1 by means of a CVD method. For this are suitable in particular CVD methods which make possible uniform application of the diamond layer forming the contact region on three-dimensional structures (see above). The hold between the diamond layer forming the contact region 6.1 and the core 10.1 is particularly strong; this arises from the fact that there is a chemical bond between core 10.1 and contact region 6. The concentration of doping agent in the contact region is preferably more than $5 \times 10^{18}$ cm$^{-3}$; in the present case a concentration of doping agent in the contact region in the region of $5 \times 10^{20}$ cm$^{-3}$ has proved to be particularly good. As preferred doping agents of the doped diamond material of the contact region, boron, sulphur, lithium or titanium here come into consideration; also possible are e.g. nitrogen, phosphorus or sp$^2$-bonded carbon in the diamond layer. The application or the doping of the diamond conductive layer took place in this case in such a way that no diffusion of the doping agents out of the diamond occurs. The diamond layer can be formed from textured or nanocrystalline diamond to produce less surface roughness.

Thus manifold diamond coatings can be produced. For easy distinction/identification it is possible to utilize the interference colors of the diamond coating.

The specific resistance of the doped diamond material forming the contact region can be set via the concentration of doping agent. Specific resistances lower than 100 Ohm cm, preferably lower than 1 Ohm cm have proved to be advantageous; in the present case it is 0.01 Ohm cm. Here, the thickness of the diamond layer applied to the core 10.1 is preferably less than 300 micrometers, preferably less than 10 micrometers. In the present case it is by particular preference between 1 and 5 micrometers.

The basic properties of the diamond forming the contact region or of the core have just been explained with the aid of FIG. 2a. It is expressly emphasized that all the details with respect to the core material, the manner of applying the conductive diamond layer to the core, the doping agents of the diamond material of the contact region, the doping agent concentration, the layer thicknesses and the specific resistances, also apply directly to the embodiments according to FIGS. 3a to 3e or 4a to 4g, insofar as nothing else is specifically said there.

FIG. 2b shows a longitudinal section as per C–C' from FIG. 1. Here can be seen how the doped diamond layer forming the contact region 6.1 is applied "like a hat" to the core 10.1 (however completely enclosing coating is also possible). Moreover, the assembly region of tip 4 of the arm can be seen.

FIG. 2c shows a further embodiment of a section as per A–A' from FIG. 1 which differs from the version shown in FIG. 2a merely in that on the inner side facing arm 3, the tip 4 of arm 2 is flattened. Otherwise, what was said in connection with FIG. 2a applies here.

FIGS. 3a to 3e show a further variant of the realization of arm tips 4 or 5 according to the basic principle of the tweezers shown in FIG. 1.

FIG. 3a shows a section as per A–A' through an arm tip 4. Structure and geometry of the core 10.2 and of the diamond conductive layer forming the contact region 6.2 correspond substantially to the embodiment shown in FIG. 2a.

In addition, however, the diamond conductive layer forming the contact region 6.2 is surrounded by an insulating layer 11.2 shaped substantially like a sickle. This insulating layer 11.2 is disposed substantially concentric with the conductive diamond layer forming the contact region 6.2, however the thickness of the insulating layer 11.2 decreases towards the inner side facing the opposite arm 3. This reduction goes so far that in the angle area delimited by marks 19, drawn in FIG. 3a, the contact region 6.2 is completely exposed, i.e. is not covered by the insulating layer 11.2.

The material of the insulating layer 11.2 is nominally non-doped-diamond, i.e. diamond which is not electrically conductive. The insulating layer 11.2 has been applied by means of a CVD method to the conductive diamond layer forming the contact region 6.2. Suitable for this purpose are again the CVD methods referred to above. The insulating layer can, however, in addition to embodiments formed from textured diamond or nanocrystalline diamond (this is particularly advantageous on account of the low roughness of the surface) also consist of DLC (diamond-like carbon). This electrically insulating layer 11.2 can here in turn be terminated differently in order to prevent the adhesion of tissue even more effectively (see here the remarks on termination in the introduction to the description, which can be applied correspondingly).

FIG. 3b shows a variant of section A–A'. Here the structure of the core or of the conductive diamond layer corresponds to the variant of FIG. 2c; in addition, the conductive diamond layer has been provided with an insulating layer 11.2', apart from the region of the flattened inner side.

FIGS. 3c and 3d show two variants of a longitudinal section as per C–C' through arm tips 4 shown in FIG. 3a or 3b. Here the basic shape corresponds in each case to the variant shown in FIG. 2b. This is supplemented by the applied insulating layer 11.2 or 11.2'. In FIG. 3c, the conductive diamond layer forming the contact region 6.2 or 6.2' is covered substantially all round with the insulating diamond layer 11.2 or 11.2', the insulating layer being merely omitted on the inner side of the arm tip 4, roughly in the region of the upper half 20, such that electrical contact can be made here.

These remarks apply substantially correspondingly to the embodiment according to FIG. 3d; however here the inner side is not covered by the insulating layer 11.2 or 11.21 over the entire height of the arm tip 4, i.e. in region 21.

Finally, FIG. 3e shows a section B–B' through two arm tips 4 and 5, which correspond to the embodiment of FIG. 3a. The configuration of tip 5 is substantially mirror-symmetrical to the above-described structure of arm tip 4. The electrical contact regions formed from doped diamond material 6.2 or 7.2, which are not covered by the insulating layer 11.2, stand directly opposite one another and can be moved towards one another by moving the arms 2 or 3, in order to grasp a piece of tissue in the space between them and pass electrical current through said tissue.

FIGS. 4a to 4g show a further embodiment of an arm tip 4 according to the invention. In its basic structure, this again corresponds first of all to the arm tip shown in FIGS. 2a to 2c. However here the insulating layer 11.3 (in respect of the material and manner of application of this layer, express reference is made to the description of FIGS. 3a to 3e) is so formed that the conductive doped diamond layer is completely electrically insulated by the insulating layer 11.3. This embodiment permits capacitive power transmission to the tissue when electricity is applied to the insulated contact region.

FIGS. 4d to 4g show a plurality of embodiments of unipolar coagulation instruments. These have differing arms 31d to 31g, to which respectively identically realized plug-in adapters are connected. Coagulation takes place in each case through contact of the arm tip with the patient's tissue to be coagulated; as counter-electrode serves e.g. an operating table on which the patient is located.

Arm 31d is realized substantially rod-shaped; a substantially round spherical electrode 32d is connected to the tip of the rod.

Arm 31e is realized substantially "sword-shaped", i.e. in the blade plane flat in comparison with the plan view shown here and tapering at the tip 32e.

Arm 31f is realized substantially needle-shaped, i.e. elongated with a comparatively sharp tip 32f.

Arm 31g is realized substantially loop-shaped, i.e. as a substantially closed curve or loop with an eye 32g.

The instruments shown in FIGS. 4d, 4e, 4f, 4g have, at the cutting points referred to as A–A', cross-sections such as have already been explained in detail in FIGS. 2a, 3a, 4a (or for non-round cross-sections e.g. 2c, 3b, 4c), such that a repeated description is dispensed with. In respect of FIGS. 4d to 4g it should be noted that here too the arms, e.g. arm,31e in FIG. 4e, can have layers of doped or non-doped diamond materials as described above. What all the embodiments have in common is that they have at the arm tips contact regions for coagulation through a flow of current.

The plug-in adapter 30 can be plugged into an instrument-holder, not shown, to produce an electrical connection and mechanical fixing. This instrument holder corresponds in structure and function first of all to the support 16 of FIG. 1, i.e. it produces in corresponding manner the electrical connection from an electrical contact connected to the control unit 12 to the contact regions of the arms (during which process, however, only the unipolar circuitry according to FIG. 5b or FIG. 6a is used). In addition, however, the instrument-holder has a handle which makes it possible for the ins instrument holder to be held in the operator's hand.

In the above-described examples the insulating layer, e.g. insulating layer 11.2, was applied to regions of the electrically conductive diamond layer. However it is naturally possible to apply this insulating layer directly if necessary also to regions of the core, e.g. 10.2. Then the above-described FIGS. 3 and 4 apply in an analogous manner.

Figure 5B:
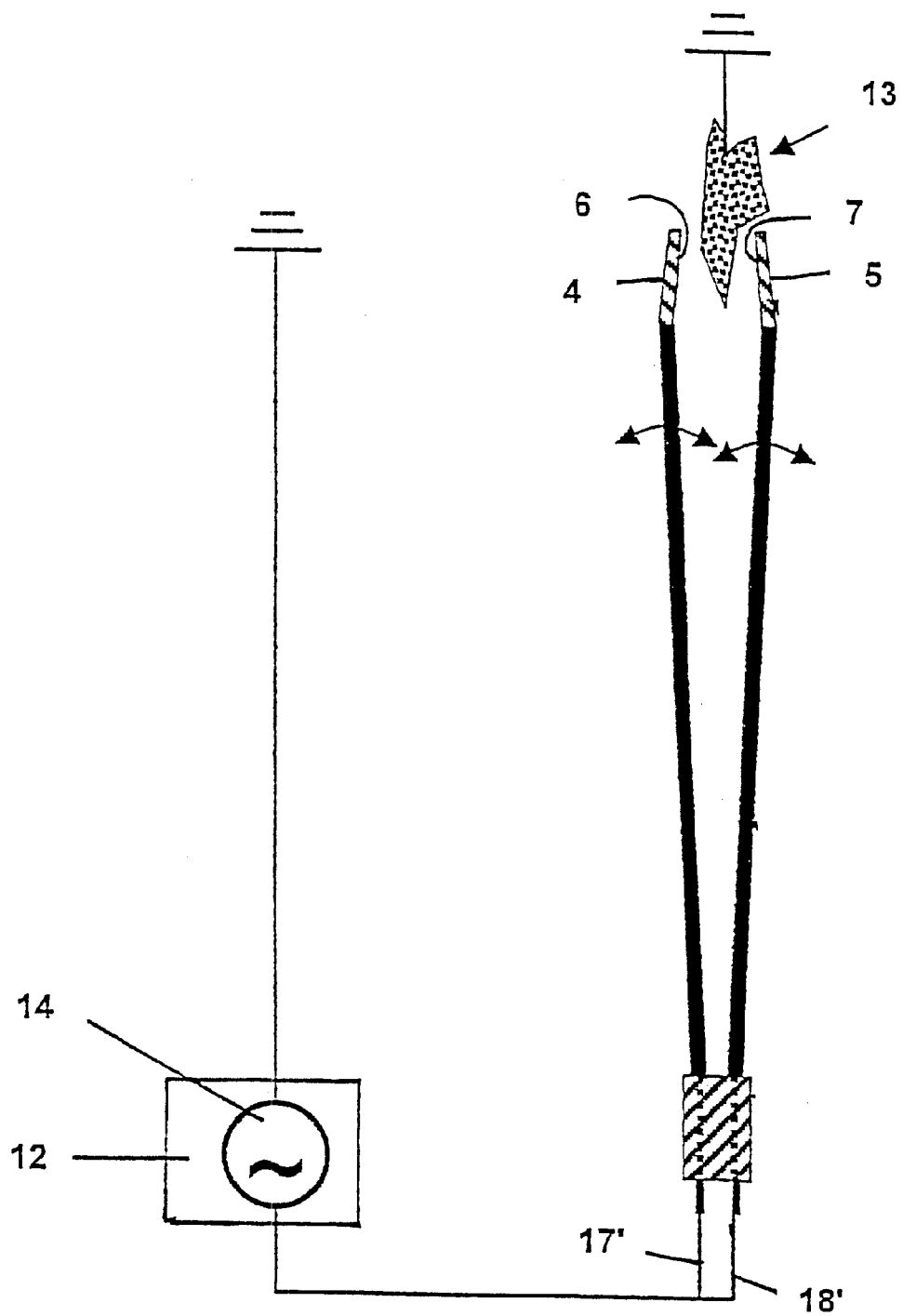
Figure 6B:
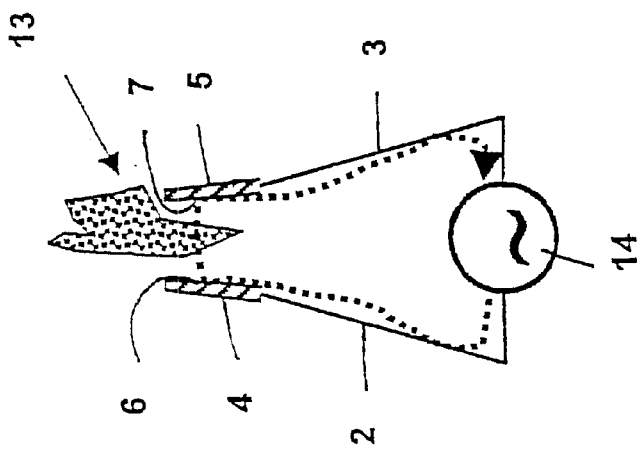
Figure 6A:
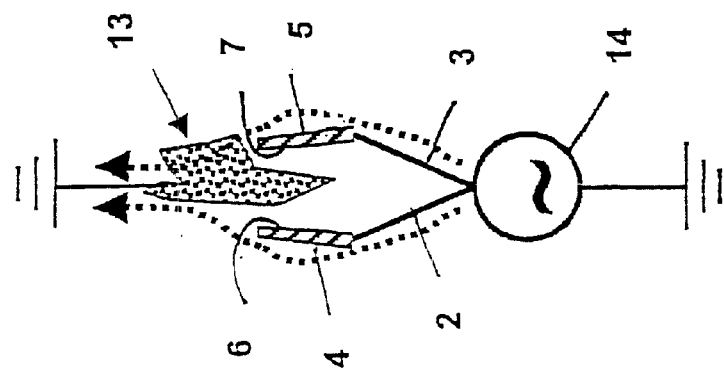

In FIGS. 5a, 5b, 6a, 6b the coagulation of tissue by means of the tweezers according to the invention is explained briefly. FIG. 5a shows a basic structure according to FIG. 1. A piece of human tissue 13 protrudes into the region between the inner sides of the arm tips 4 and 5. The control unit 12 is equipped with a high-frequency generator 14 to generate unmodulated and modulated high-frequency currents through the electrically conductive contact regions disposed on the inner sides of the arm tips 4 and 5. Arms 2 and 3 are here disposed moveable towards one another such that a piece of tissue 13 to be grasped by arm tips 4 and 5 can be securely clamped against the inner sides of arm tips 4 and 5.

FIG. 5a shows the structure of the tweezers according to the invention in bipolar operation (arms 2 and 3 are electrically insulated from one another in their support 16). Here the tweezers 2 have poles which lead on the one hand from the contact region 6 over the remaining arm 2 and line 17 and on the other hand over the contact region 7, the remaining arm 3 and line 18 to the control unit 12. The coagulation of the grasped tissue 13 in the bipolar operation can be read from the sketch in FIG. 6b. It can be seen that the current path or flow is closed (see broken line). Proceeding from the high-frequency generator, the current flows, e.g. via arm 2 and contact region 6, through the human tissue 13 to contact region 7 of arm 3 and back again to the high-frequency generator. Thus merely the region to be coagulated in a very limited space is exposed to the flow of current. More precise tissue action is possible if a partially insulated pair of tweezers is used, e.g. as per FIGS. 3b, c. Then there is merely current conduction between the inner surfaces of the tips; surrounding tissue is not damaged.

Alternatively, however, unipolar operation is also possible (in FIGS. 4d to 4g exclusively).

FIG. 5b shows in this connection the basic circuitry of the tweezers according to the invention. Here, the electrical lines 17' and 18', which are electrically connected to the contact regions 6 and 7, are electrically combined to form a single line which then opens out into the high-frequency generator 14 of the control unit 12. For this purpose, the high-frequency generator 14 is earthed on the other side. The human or animal tissue 13 to be coagulated is also earthed; special arrangements have to be made for this in order to earth the human/animals lying e.g. on an operating table. Here lines 17' and 18' could also be combined into a single part.

FIG. 6a shows a schematic diagram of the current path or flow during unipolar operation of the tweezers according to the invention as shown in FIG. 5b. Here the current flows starting from the high-frequency generator through the contact regions which have the same electrical polarity and through the tissue to be coagulated, which has been grasped by the tweezers or touched by the contact regions, e.g. into the operating table. This earthed operating table contains a correspondingly "neutral electrode" which in turn is connected on the other side to the high-frequency generator. The flow of current is again represented by a broken line in FIG. 6a.

For capacitive coupling (see also FIGS. 4a to 4c), the same basically applies; however, there is here no net current flow but merely a heat flow through capacitive energy transfer.

Figure 7B:
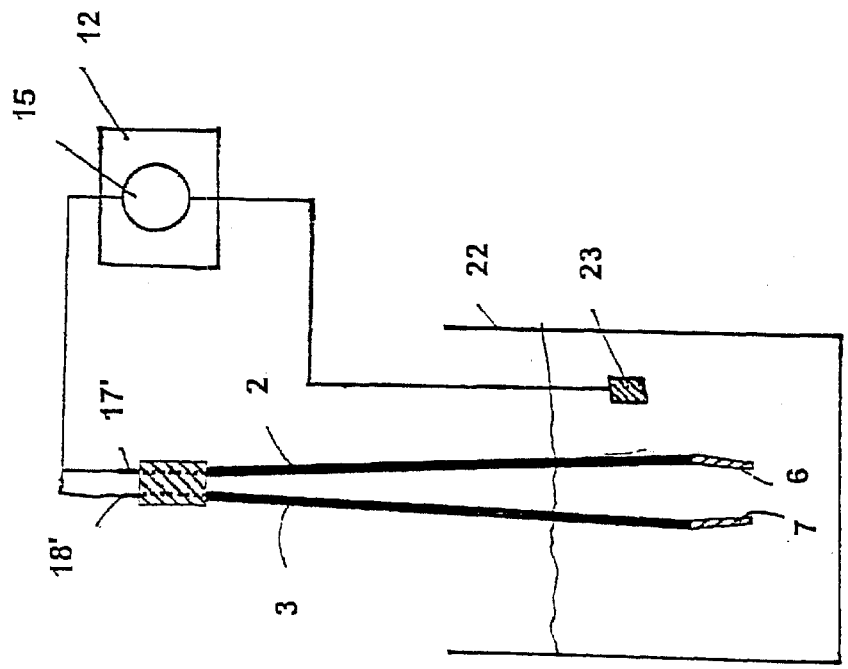
Figure 7A:
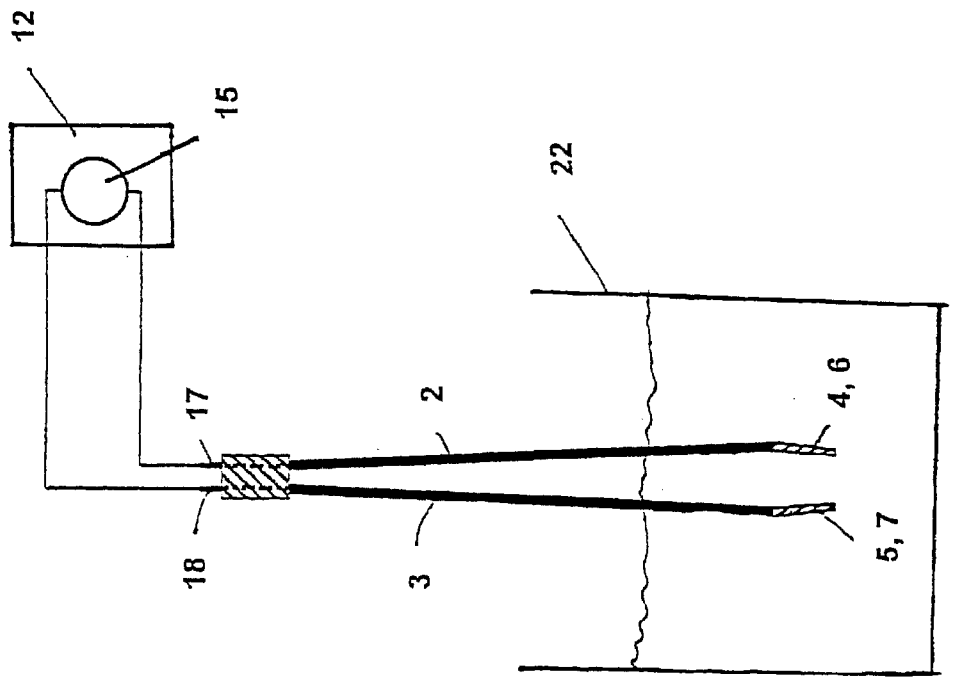

FIGS. 7a and 7b show the electrochemical cleaning of a pair of tweezers according to the invention provided with tissue adhesions.

FIG. 7a shows an immersing basin 22 which can be filled with liquid and which belongs to the control 12 unit or can be connected to same. In the present case, the immersing basin is preferably filled with distilled water, to which e.g. sulphuric acid has been added, to set the electrical conductivity (other additives are possible, see above). The tips 4 and 5 of the arms 2 and 3 are dipped into the liquid of the immersing basin 22. The tweezers are connected up in a bipolar manner, i.e. one pole of the tweezers, starting from contact region 6, leads via supply line 17 to the control unit, the other pole via contact region 7 and supply line 18 to the control unit 12 (see analogously, FIG. 5a). The control unit 12 contains a voltage source 15 which can optionally generate d.c. or a.c. voltage. The voltage which can be generated from this voltage source is around 0 to 1000 V, preferably 0 to 10 V, by particular preference 1 to 5 V. At the contact regions 6 and 7 provided with tissue adhesions, current densities of up to 10 ampere per $CM^2$ are achieved.

In this electrochemical cleaning of the contact regions or of the arm tips 4 and 5, particularly advantageous properties of electrically conductive diamond emerge. The contact region formed from diamond is not altered by the flow of current; there is no possible deterioration as would be the case with metal electrodes. But even during pre-cleaning, the diamond shows particularly favorable properties since the mechanical or chemical pre-cleaning can take place more gently as a result of the lower tendency to adhere to the diamond. Moreover the diamond contact regions could also be cleaned by means of conventional methods and would be more robust than metal contacts.

When a voltage is applied to the contacts 17 and 18, there is "self-cleaning" of the diamond contact regions. It has emerged here that when direct current is applied, the positive pole or the anode is cleaned particularly well. For adequate cleaning of both contact regions during cleaning in the bipolar operation shown here, it is necessary therefore to reverse the polarity after a certain time. This can e.g. also be achieved by using an a.c. voltage.

FIG. 7b shows the cleaning of tweezers according to the invention in unipolar operation (the cleaning of other surgical instruments in the sense of the invention. For instances the coagulation instruments according to FIGS. 4d to 4g, comes about in a corresponding manner. It should be noted that here, respectively, only one arm is provided which is poled against the counter-electrode 23). Here, the structure is substantially identical to that described in FIG. 7a; however in the present case the electrical lines 18' and 17' are combined to form a single pole, which leads to the voltage source 15 of the control unit 12. This voltage source is connected on the other side to the additional electrode 23 which is also introduced into the liquid of the immersing basin 22 (in a further embodiment it is possible to configure the wall of the immersing basin itself as the counter-electrode 23 or to provide the electrode in this wall). In the electrochemical cleaning shown here the contact regions 6 and 7 thus have the same polarity (see also FIG. 5b). Consequently, the cleaning of both tips of the tweezers simultaneously is here possible. In principle both d.c. and a.c. voltage can be used. The cleaning of the unipolar instruments according to 4d to 4g takes place in an analogous manner; here the two-armed insertion into the mounting 16 is replaced by the holder for the electrodes according to 4d to 4g.

In addition to the types of cleaning described in FIGS. 7a and 7b, other types are also possible for the surgical instruments according to the invention. In the above-described variants, the voltage was applied directly to the contact regions of the surgical instrument ("active" electrochemical cleaning). However, "passive" chemical cleaning is also possible in which two immersing bath electrodes, between which a voltage is built up, are dipped into a bath of liquid and the surgical instrument is dipped into this liquid bath for cleaning, preferably in the region between the two immersing bath electrodes. It can here be particularly recommended for at least one of the immersing bath electrodes to consist of electrically conductive diamond or be coated with same.

The electrochemical cleaning can also be further accelerated or improved by additional measures. Acceleration of the cleaning process occurs when a heating device provided in the immersing basin heats up the liquid in the immersing basin 22 (preferably up to 90° C.). In addition, the immersing basin can also have a device for generating ultrasound in order to apply ultrasound to the liquid and thus acceleration of the cleaning process can be achieved. Acceleration can also be achieved by applying air/gas bubbles to the cleaning liquid or by stirring.

The method described above is also suitable for (pre) sterilization. For the contaminated regions which are not formed from the doped diamond material, an additional cleaning is still necessary.

Figure 8:
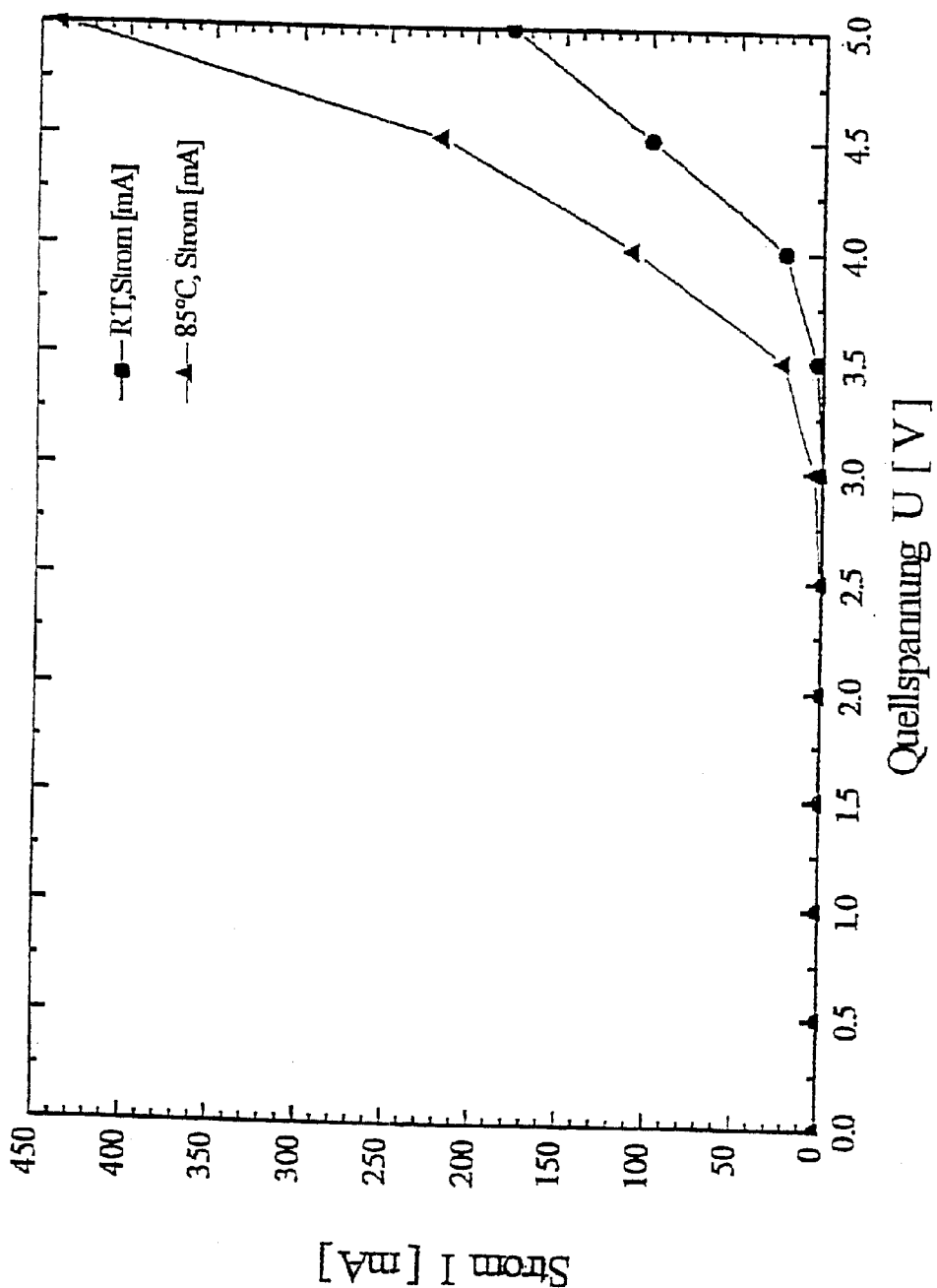

Finally, FIG. 8 shows an electrolysis current curve for tweezers according to the invention. This has contact regions which consist of a diamond material doped with boron which is applied to a core formed from niobium. Despite relatively low current density, a good cleaning effect was produced.

What is claimed is:

1. Instrument assembly for surgical purposes, especially for coagulation, the instrument assembly comprising:
   at least one arm, the at least one arm having electrical contact regions, said contact regions electrically connectible to a control unit for acting on tissue located in the vicinity by applying electricity to the contact region, and the contact region consists of doped diamond to produce the electrical conductivity, wherein the contact region has a concentration of a doping agent higher than $5 \times 10^{18}$ cm$^{-3}$.

2. Instrument assembly according to claim 1, wherein the instrument assembly has two arms movable towards one another, e.g. in the shape of tweezers, each arm having a tip, the tip of at least one arm having the electrical contact region formed from doped diamond to touch and grasp the tissue for the purpose of coagulation.

3. Instrument assembly according to claim 2, wherein at least the tips of the arms have a core to which the doped diamond forming the contact regions is applied.

4. Instrument assembly according to claim 3, wherein the material of the core is electrically conductive, in particular that the core is formed from a refractory metal, preferably titanium, tungsten, niobium, tantalum, iridium or alloys of these metals, or in that the core is Zr, graphite or carbon-fibre reinforced carbon.

5. Instrument assembly according to claim 3 wherein the contact region formed from doped diamond is applied to the core by means of diamond CVD.

6. Instrument assembly according to claim 5, wherein the contact region formed from doped diamond is applied by means of hot-filament CVD, microwave CVD or microwave CVD supported by electron cyclotron resonance.

7. Instrument assembly according to claim 3, wherein there is a chemical bond between the core and the contact region.

8. Instrument assembly according to claim 3, wherein an insulating material is applied to regions of the core.

9. Instrument assembly according to claim 8, wherein the insulating material is applied on the doped diamond, the contact regions being omitted.

10. Instrument assembly according to claim 8, wherein the insulating material completely covers the doped diamond.

11. Instrument assembly according to claim 8, wherein the insulating material comprises a nominally non-doped diamond layer, applied by the CVD method and formed from textured diamond, nanocrystalline diamond or DLC (diamond-like carbon).

12. Instrument assembly according to claim 10, wherein the cleaning liquid contains distilled water.

13. Instrument assembly according to claim 12, wherein the liquid is distilled water with additives such as sulphuric acid or the like to increase the electrical conductivity.

14. Instrument assembly according to claim 12, wherein the liquid has distilled water with cleaning agents.

15. Instrument assembly according to claim 1, the concentration of the doping agent in the contact region is $5 \times 10^{20}$ cm$^{-3}$.

16. Instrument assembly according to claim 1, wherein the specific resistance of the doped diamond of the contact regions is lower than 100 Ohm cm, preferably lower than 1 Ohm cm, by particular preference lower than 0.01 Ohm cm.

17. Instrument assembly according to claim, 1 wherein the doping agent of the doped diamond of the contact regions is boron, sulphur, nitrogen, lithium, phosphorus or titanium.

18. Instrument assembly according to claim 1, wherein the layer thickness of the contact region is less than 300 micrometers, preferably less than 10 micrometers, by particular preference 1 to 5 micrometers.

19. Instrument assembly according to claim 1, wherein the doped diamond consists of DLC, nanocrystalline diamond or textured diamond applied by a CVD method.

20. Instrument assembly according to claim 1, further comprising a control unit equipped with a source of d.c. or a.c. voltage, preferably with a high-frequency generator to generate unmodulated and modulated high-frequency currents through the contact regions.

21. Instrument assembly according to claim 1, further comprising a means for cleaning a portion of the instrument assembly, said means for cleaning includes an immersing basin for filling with cleaning liquid, for dipping the contact regions into the liquid, and wherein another portion of the instrument assembly is connected to a voltage source to apply a d.c. or a.c. voltage to the contact regions dipped into the liquid, and that the voltages generated from the voltage source are 0 to 10 V.

22. Instrument assembly according to claim 21, wherein the voltages generated from the voltage source are preferably 1 to 5 V.

23. Instrument assembly according to claim 21, wherein the immersing basin has a heating device for heating up the liquid.

24. Instrument assembly according to claim 21, wherein the immersing basin has an ultrasound generator to apply ultrasound to the liquid.

25. Instrument assembly according to claim 1, wherein two contact regions are provided and the two contact regions have one of opposite polarity and the same polarity.

26. Instrument assembly according to claim 1, wherein the polarity of the contact regions is different during a coagulation operation and during a cleaning operation.

27. Method of cleaning the contact regions of the instrument assembly according to, claim 1, the steps comprising:

providing a basin having electrically conductive liquid therein;

dipping said contact regions into the electrically conductive liquid for electrochemical cleaning; and applying one of a d.c. and a.c. voltage with a voltage from 0 to 10 V to the contact regions to produce a flow of current through said contact regions.

* * * * *

UNITED STATES PATENT AND TRADEMARK OFFICE
CERTIFICATE OF CORRECTION

PATENT NO.    : 6,558,380 B2
DATED         : May 6, 2003
INVENTOR(S)   : Lingenfelder et al.

It is certified that error appears in the above-identified patent and that said Letters Patent is hereby corrected as shown below:

<u>Title page,</u>
Item [73], "Assignee" should read -- Assignees -- and insert the following assignee:
-- Fraunhofer-Gesellschaft zur Förderung der angewandten Forschung e. V., München (DE) --.

Signed and Sealed this

Twenty-sixth Day of August, 2003

JAMES E. ROGAN
*Director of the United States Patent and Trademark Office*